United States Patent
Chan et al.

(10) Patent No.: US 8,551,786 B2
(45) Date of Patent: Oct. 8, 2013

(54) SYSTEMS AND METHODS FOR ENHANCING FLUORESCENT DETECTION OF TARGET MOLECULES IN A TEST SAMPLE

(75) Inventors: Warren Che Wor Chan, Toronto (CA); Travis Leon Jennings, San Diego, CA (US); Jesse M. Klostranec, Toronto (CA)

(73) Assignee: FIO Corporation, Toronto, Ontario (CA)

( * ) Notice: Subject to any disclaimer, the term of this patent is extended or adjusted under 35 U.S.C. 154(b) by 27 days.

(21) Appl. No.: 12/668,264

(22) PCT Filed: Jul. 9, 2008

(86) PCT No.: PCT/CA2008/001264
§ 371 (c)(1),
(2), (4) Date: Nov. 4, 2010

(87) PCT Pub. No.: WO2009/006739
PCT Pub. Date: Jan. 15, 2009

(65) Prior Publication Data
US 2011/0053278 A1    Mar. 3, 2011

Related U.S. Application Data

(60) Provisional application No. 60/948,643, filed on Jul. 9, 2007.

(51) Int. Cl.
*G01N 21/76* (2006.01)
*G01N 21/75* (2006.01)
*G01N 33/53* (2006.01)
*G01N 33/543* (2006.01)

(52) U.S. Cl.
USPC ............. 436/172; 436/64; 436/164; 436/805; 436/813; 436/501; 436/518; 436/531; 436/533; 436/534; 422/82.08; 435/6.14; 435/7.1; 435/287.2; 435/288.7; 435/808; 435/968; 356/317; 250/458.1; 250/459.1

(58) Field of Classification Search
USPC ......... 436/501, 518, 531, 532, 533, 534, 535, 436/64, 164, 172, 805, 811, 813; 422/82.05, 82.08, 82.09; 435/6.1, 6.11, 435/6.14, 6.19, 7.1, 287.1, 287.2, 288.7, 435/808, 968; 356/432, 317; 250/458.1, 250/459.1
See application file for complete search history.

(56) References Cited

U.S. PATENT DOCUMENTS 5,244,630 A    9/1993  Khalil et al.
5,518,883 A *  5/1996  Soini ............................ 435/6.11
(Continued)

FOREIGN PATENT DOCUMENTS

CA    2061574    8/1992
CA    2021587    4/2003
(Continued)

OTHER PUBLICATIONS

Wang et al. Bioconjugate Chemistry, vol. 16, 2005, pp. 194-199.*
(Continued)

*Primary Examiner* — Maureen Wallenhorst
(74) *Attorney, Agent, or Firm* — Jennifer E. Lacroix, Esq.; DLA Piper LLP US

(57) ABSTRACT

Systems and methods for enhancing fluorescent detection of target molecules in a test sample are for use with an irradiating device. First fluorophores are provided for absorption of EMF radiation, and emission of a first signal. Second fluorophores are provided for partial absorption of the first signal, and emission of a second signal distinguishable from the first signal. The fluorophores are combined with the test sample, and secured to the target molecules and relative to one another. After the first fluorophores receive the EMF radiation from the irradiating device, the first signal is detected, together with the second spectral signal if the target molecules are present in the test sample.

27 Claims, 8 Drawing Sheets

(56) References Cited

U.S. PATENT DOCUMENTS

| | | |
|---|---|---|
| 5,662,824 A | 9/1997 | Sang et al. |
| 5,714,390 A | 2/1998 | Hallowitz et al. |
| 5,786,219 A | 7/1998 | Zhang et al. |
| 5,817,458 A | 10/1998 | King et al. |
| 5,837,442 A | 11/1998 | Tsang |
| 6,011,252 A | 1/2000 | Jensen |
| 6,022,500 A | 2/2000 | John et al. |
| 6,066,243 A | 5/2000 | Anderson et al. |
| 6,100,541 A | 8/2000 | Nagle et al. |
| 6,103,379 A | 8/2000 | Margel et al. |
| 6,114,038 A | 9/2000 | Castro et al. |
| 6,119,953 A | 9/2000 | Ganan-Calvo et al. |
| 6,172,193 B1 | 1/2001 | Primi et al. |
| 6,174,469 B1 | 1/2001 | Ganan-Calvo |
| 6,261,779 B1 | 7/2001 | Barbera-Guillem et al. |
| 6,274,323 B1 | 8/2001 | Bruchez et al. |
| 6,309,701 B1 | 10/2001 | Barbera-Guillem |
| 6,316,781 B1 | 11/2001 | Nagle et al. |
| 6,319,607 B1 | 11/2001 | Barbera-Guillem et al. |
| 6,333,110 B1 | 12/2001 | Barbera-Guillem |
| 6,340,588 B1 | 1/2002 | Nova et al. |
| 6,353,475 B1 | 3/2002 | Jensen et al. |
| 6,357,670 B2 | 3/2002 | Ganan-Calvo |
| 6,399,952 B1 | 6/2002 | Maher et al. |
| 6,409,900 B1 | 6/2002 | Parce et al. |
| 6,413,401 B1 | 7/2002 | Chow et al. |
| 6,430,512 B1 | 8/2002 | Gallagher |
| 6,468,808 B1 | 10/2002 | Nie et al. |
| 6,494,830 B1 | 12/2002 | Wessel |
| 6,498,353 B2 | 12/2002 | Nagle et al. |
| 6,504,607 B2 | 1/2003 | Jensen et al. |
| 6,506,609 B1 | 1/2003 | Wada et al. |
| 6,514,399 B1 | 2/2003 | Parce et al. |
| 6,524,793 B1 | 2/2003 | Chandler et al. |
| 6,528,165 B2 | 3/2003 | Chandler |
| 6,544,732 B1 | 4/2003 | Chee et al. |
| 6,548,171 B1 | 4/2003 | Barbera-Guillem et al. |
| 6,548,264 B1 | 4/2003 | Tan et al. |
| 6,554,202 B2 | 4/2003 | Ganan-Calvo |
| 6,576,155 B1 | 6/2003 | Barbera-Guillem |
| 6,592,821 B1 | 7/2003 | Wada et al. |
| 6,592,822 B1 | 7/2003 | Chandler |
| 6,630,307 B2 | 10/2003 | Bruchez et al. |
| 6,632,655 B1 | 10/2003 | Mehta et al. |
| 6,649,138 B2 | 11/2003 | Adams et al. |
| 6,673,662 B2 | 1/2004 | Singh |
| 6,680,211 B2 | 1/2004 | Barbera-Guillem et al. |
| 6,699,723 B1 | 3/2004 | Weiss et al. |
| 6,720,411 B2 | 4/2004 | Mirkin et al. |
| 6,734,420 B2 | 5/2004 | Empedocles et al. |
| 6,740,491 B2 | 5/2004 | Mirkin et al. |
| 6,752,966 B1 | 6/2004 | Chazan |
| 6,759,235 B2 | 7/2004 | Empedocles et al. |
| 6,767,706 B2 | 7/2004 | Quake et al. |
| 6,772,070 B2 | 8/2004 | Gilmanshin et al. |
| 6,773,812 B2 | 8/2004 | Chandler et al. |
| 6,778,724 B2 | 8/2004 | Wang et al. |
| 6,787,088 B2 | 9/2004 | Parce et al. |
| 6,835,326 B2 | 12/2004 | Barbera-Guillem |
| 6,872,249 B2 | 3/2005 | Peng et al. |
| 6,881,537 B1 | 4/2005 | Goudsmit et al. |
| 6,881,821 B2 | 4/2005 | Simmonds et al. |
| 6,890,764 B2 | 5/2005 | Chee et al. |
| 6,905,885 B2 | 6/2005 | Colsten et al. |
| 6,966,880 B2 | 11/2005 | Boecker et al. |
| 6,978,212 B1 | 12/2005 | Sunshine |
| 6,986,837 B2 | 1/2006 | Chow et al. |
| 7,037,729 B2 | 5/2006 | Nie et al. |
| 7,041,362 B2 | 5/2006 | Barbera-Guillem |
| 7,069,191 B1 | 6/2006 | Moore |
| 7,077,328 B2 | 7/2006 | Kirchnaswamy et al. |
| 7,079,241 B2 | 7/2006 | Empedocles et al. |
| 7,166,475 B2 | 1/2007 | Colyer et al. |
| 7,171,983 B2 | 2/2007 | Chien et al. |
| 7,192,785 B2 | 3/2007 | Nie et al. |
| 7,243,670 B2 | 7/2007 | Witt et al. |
| 7,252,928 B1 | 8/2007 | Hafeman et al. |
| 7,267,799 B1 | 9/2007 | Borich et al. |
| 2001/0027918 A1 | 10/2001 | Parce et al. |
| 2001/0028055 A1 | 10/2001 | Fafard et al. |
| 2001/0046602 A1 | 11/2001 | Chandler et al. |
| 2001/0055764 A1 | 12/2001 | Empedocles et al. |
| 2002/0009728 A1 | 1/2002 | Bittner et al. |
| 2002/0022273 A1 | 2/2002 | Empedocles et al. |
| 2002/0031783 A1 | 3/2002 | Empedocles et al. |
| 2002/0037499 A1 | 3/2002 | Quake et al. |
| 2002/0045045 A1 | 4/2002 | Adams et al. |
| 2002/0048425 A1 | 4/2002 | McBride et al. |
| 2002/0051971 A1 | 5/2002 | Stuelpnagel et al. |
| 2002/0059030 A1 | 5/2002 | Otworth et al. |
| 2002/0066401 A1 | 6/2002 | Peng et al. |
| 2002/0081617 A1* | 6/2002 | Buranda et al. ............ 435/6 |
| 2002/0118355 A1 | 8/2002 | Worthington et al. |
| 2002/0144644 A1 | 10/2002 | Zehnder et al. |
| 2002/0164271 A1 | 11/2002 | Ho |
| 2002/0182609 A1 | 12/2002 | Arcot |
| 2003/0003441 A1 | 1/2003 | Colston et al. |
| 2003/0017264 A1 | 1/2003 | Treadway et al. |
| 2003/0026740 A1 | 2/2003 | Staats |
| 2003/0073086 A1 | 4/2003 | Guire et al. |
| 2003/0099940 A1 | 5/2003 | Empedocles et al. |
| 2003/0132538 A1 | 7/2003 | Chandler |
| 2003/0148530 A1 | 8/2003 | Lauks |
| 2003/0148544 A1 | 8/2003 | Nie et al. |
| 2003/0157327 A1 | 8/2003 | Barbera-Guillem et al. |
| 2003/0165951 A1 | 9/2003 | Bruchez, Jr. et al. |
| 2003/0170613 A1 | 9/2003 | Straus et al. |
| 2003/0172043 A1 | 9/2003 | Guyon et al. |
| 2003/0175773 A1 | 9/2003 | Chee et al. |
| 2003/0176183 A1 | 9/2003 | Drucker et al. |
| 2003/0177038 A1 | 9/2003 | Rao |
| 2003/0177941 A1 | 9/2003 | Barbera-Guillem |
| 2003/0190628 A1 | 10/2003 | Nakao et al. |
| 2003/0194350 A1 | 10/2003 | Stamatelos et al. |
| 2004/0009341 A1 | 1/2004 | Naasani |
| 2004/0067485 A1 | 4/2004 | Mayes et al. |
| 2004/0072428 A1 | 4/2004 | Sato et al. |
| 2004/0096363 A1 | 5/2004 | Porter |
| 2004/0101621 A1 | 5/2004 | Adams et al. |
| 2004/0106218 A1 | 6/2004 | Wang et al. |
| 2004/0118684 A1 | 6/2004 | Wainright et al. |
| 2004/0147031 A1 | 7/2004 | Nakao |
| 2004/0176704 A1 | 9/2004 | Stevens et al. |
| 2004/0203170 A1 | 10/2004 | Barbera-Guillem |
| 2004/0204633 A1 | 10/2004 | Rentea et al. |
| 2004/0229261 A1 | 11/2004 | Young |
| 2004/0241424 A1 | 12/2004 | Barbera-Guillem |
| 2004/0241752 A1 | 12/2004 | Anderson et al. |
| 2004/0247861 A1 | 12/2004 | Naasani |
| 2004/0248167 A1 | 12/2004 | Quake et al. |
| 2004/0266022 A1 | 12/2004 | Sundararajan et al. |
| 2004/0267568 A1 | 12/2004 | Chandler et al. |
| 2005/0004346 A1 | 1/2005 | Dziegiel et al. |
| 2005/0009002 A1 | 1/2005 | Chen et al. |
| 2005/0011764 A1 | 1/2005 | Berndt et al. |
| 2005/0014134 A1 | 1/2005 | West et al. |
| 2005/0032047 A1 | 2/2005 | Simmonds et al. |
| 2005/0043894 A1 | 2/2005 | Fernandez et al. |
| 2005/0059030 A1 | 3/2005 | Bao et al. |
| 2005/0071199 A1 | 3/2005 | Riff |
| 2005/0106257 A1 | 5/2005 | Albayrak |
| 2005/0112277 A1 | 5/2005 | Banerjee et al. |
| 2005/0120946 A1 | 6/2005 | Hines et al. |
| 2005/0128479 A1 | 6/2005 | Gilbert et al. |
| 2005/0164264 A1 | 7/2005 | Shipwash |
| 2005/0214536 A1 | 9/2005 | Schrier et al. |
| 2005/0221296 A1 | 10/2005 | Simmonds et al. |
| 2005/0227370 A1 | 10/2005 | Ramel et al. |
| 2005/0239118 A1 | 10/2005 | Goudsmit et al. |
| 2005/0260660 A1* | 11/2005 | van Dongen et al. ............ 435/6 |
| 2006/0008921 A1 | 1/2006 | Daniels et al. |
| 2006/0012784 A1 | 1/2006 | Ulmer |
| 2006/0014040 A1 | 1/2006 | Peng et al. |
| 2006/0019098 A1 | 1/2006 | Chan et al. |

| | | | |
|---|---|---|---|
| 2006/0029267 | A1 | 2/2006 | Frost et al. |
| 2006/0046330 | A1 | 3/2006 | Chen et al. |
| 2006/0063160 | A1 | 3/2006 | West et al. |
| 2006/0068203 | A1 | 3/2006 | Ying et al. |
| 2006/0078490 | A1 | 4/2006 | Shih et al. |
| 2006/0105335 | A1 | 5/2006 | Daehne et al. |
| 2006/0152372 | A1 | 7/2006 | Stout |
| 2006/0169800 | A1 | 8/2006 | Rosell |
| 2006/0172318 | A1* | 8/2006 | Medinz et al. .............. 435/6 |
| 2006/0173715 | A1 | 8/2006 | Wang |
| 2006/0194030 | A1 | 8/2006 | Barbera-Guillem |
| 2007/0020779 | A1 | 1/2007 | Stavis et al. |
| 2007/0031283 | A1 | 2/2007 | Davis et al. |
| 2007/0081920 | A1 | 4/2007 | Murphy et al. |
| 2007/0184453 | A1* | 8/2007 | Sagner et al. .............. 435/6 |

FOREIGN PATENT DOCUMENTS

| | | |
|---|---|---|
| CA | 2518352 | 3/2005 |
| EP | 1315099 | 5/2003 |
| JP | 2002-271 | 1/2002 |
| JP | 2005-508493 | 3/2005 |
| WO | 99/19000 | 4/1999 |
| WO | 99/36564 | 7/1999 |
| WO | 99/64840 | 12/1999 |
| WO | 99/66318 | 12/1999 |
| WO | 00/13580 | 3/2000 |
| WO | 00/28598 | 5/2000 |
| WO | 00/70080 | 11/2000 |
| WO | 01/20533 | 3/2001 |
| WO | 01/89585 | 11/2001 |
| WO | 01/93754 | 12/2001 |
| WO | 02/04484 | 1/2002 |
| WO | 03/003015 | 1/2003 |
| WO | 2004/008550 | 1/2004 |
| WO | 2004/040319 | 5/2004 |
| WO | 2005/023923 | 3/2005 |
| WO | 2005/031802 | 4/2005 |
| WO | 2005/052996 | 6/2005 |
| WO | 2005/053649 | 6/2005 |
| WO | 2005/061095 | 7/2005 |
| WO | 2006/033732 | 3/2006 |
| WO | 2006/045004 | 4/2006 |
| WO | 2006/072306 | 7/2006 |
| WO | 2006/132953 | 12/2006 |
| WO | 2007/011622 | 1/2007 |
| WO | 2007/066126 * | 6/2007 |
| WO | 2007/093043 * | 8/2007 |
| WO | 2008/089155 | 7/2008 |
| WO | 2008/147382 | 12/2008 |
| WO | 2009/059404 | 5/2009 |

OTHER PUBLICATIONS

Alivisatos, A.P., Perspectives on the Physical Chemistry of Semiconductor Nanocrystals, Journal of Physical Chemistry, 1996, pp. 13226-13239, vol. 100, No. 31, American Chemical Society, USA.

Bakalova, Rurniana et al., Quantum dot-conjugated hybridization probes for preliminary screening of siRNA sequences, Journal of the American Chemical Society, Aug. 1, 2005, pp. 11328-11335, vol. 127, No. 32, American Chemical Society, USA.

Boldt, Klaus et al., Comparative Examination of the Stability of Semiconductor Quantum Dots in Various Biochemical Buffers, Journal of Physical Chemistry B, 2006, pp. 1959-1963, vol. 110, No. 5, American Chemical Society, USA.

Branch, Mary Ann et al., A Subspace, Interior, and Conjugate Gradient Method for Large-Scale Bound-Constrained Minimization Problems, SIAM J. Sci. Comput., Aug. 3, 1999, pp. 1-23, vol. 21, No. 1, Society for Industrial and Applied Mathematics.

Bruchez, Marcel Jr. et al., Semiconductor Nanocrystals as Fluorescent Biological Labels, Science, Sep. 25, 1998, pp. 2013-2015, vol. 281, American Association for the Advancement of Science, USA.

Burns, Mark A. et al., An Integrated Nanoliter DNA Analysis Device, Science, Oct. 16, 1998, pp. 484-487, vol. 282, No. 5388, American Association for the Advancement of Science, USA.

Chabinyc, Michael L. et al., An Integrated Fluorescence Detection System in Poly(dimethylsiloxane) for Microfluidic Applications, Analytical Chemistry, Sep. 15, 2001, pp. 4494-4498, vol. 73, No. 18, American Chemical Society, USA.

Chan, Eugene Y. et al., DNA Mapping Using Microfluidic Stretching and Single-Molecule Detection of Fluorescent Site-Specific Tags, Genome Research, 2004, pp. 1137-1146, vol. 14, Cold Spring Harbour Laboratory Press, USA.

Chan, Warren C.W. et al., Luminescent quantum dots for multiplexed biological detection and imaging, Current Opinion in Biotechnology, 2002, pp. 40-46, vol. 13, Elsevier Science Ltd.

Chan, Warren C.W. et al., Quantum Dot Bioconjugates for Ultrasensitive Nonisotopic Detection, Science, Sep. 25, 1998, pp. 2016-2018, vol. 281, American Association for the Advancement of Science, USA.

Chou, Hou-Pu et al., A microfabricated device for sizing and sorting DNA molecules, PNAS—Proceedings of the National Academy of Sciences of the United States of America, Jan. 1999, pp. 11-13, vol. 96, The National Academy of Sciences, USA.

Dabbousi, B.O. et al., (CdSe)ZnS Core-Shell Quantum Dots: Synthesis and Characterization of a Size Series of Highly Luminescent Nanocrystallites, Journal of Physical Chemistry B, 1997, pp. 9463-9475, vol. 101, No. 46, American Chemical Society, USA.

Duffy, D.C. et al., Rapid Prototyping of Microfulidic Systems in Poly(dimethylsiloxane), Analytical Chemistry, Dec. 1, 1998, pp. 4974-4984, vol. 70, No. 23, American Chemical Society, USA.

Eisenstein, Michael, Technology Feature: Protein Arrays—Growing pains, Losing the Label, an Apt Solution? & (Almost) No Assembly Required, Nature, Dec. 14, 2006, pp. 959-962, vol. 444, Nature Publishing Group, USA.

Fournier-Bidoz, Sebastien et al., Facile and Rapid One-Step Mass Preparation of Quantum-Dot Barcodes, Angewandte Chemie International Edition, 2008, pp. 5577-5581, vol. 47, No. 30, Wiley-VCH Verlag GmbH & Co. KGaA, Weinheim.

Fu, Anne Y. et al., A microfabricated fluorescence-activated cell sorter, Nature Biotechnology, Nov. 1999, pp. 1109-1111, vol. 17, Nature America Inc., USA.

Fu, Lung-Ming et al., Multiple injection techniques for microfluidic sample handling, Electrophoresis, 2003, pp. 3026-3032, vol. 24, Wiley-VCH Verlag GmbH & Co. KGaA, Weinheim.

Gao, Xiaohu et al., In vivo cancer targeting and imaging with semiconductor quantum dots, Nature Biotechnology, Jul. 18, 2004, pp. 969-976, vol. 22, No. 8, Nature Publishing Group, USA.

Gao, Xiaohu et al., Quantum Dot-Encoded Mesoporous Beads with High Brightness and Uniformity: Rapid Readout Using Flow Cytometry, Analytical Chemistry, Apr. 15, 2004, pp. 2406-2410, vol. 76, No. 8, American Chemical Society, USA.

Gao, Xiaohu et al., Quantum-dot nanocrystals for ultrasensitive biological labelling and mulitcolor optical encoding, Journal of Biomedical Optics, Oct. 2002, pp. 532-537, vol. 7, No. 4, SPIE.

Gaponik, Nikolai et al., Toward Encoding Combinatorial Libraries: Charge-Driven Microencapsulation of Semiconductor Nanocrystals Luminescing in the Visible and Near IR, Advanced Materials, Jun. 18, 2002, pp. 879-882, vol. 14, No. 12, Wiley-VCH Verlag GmbH, Weinheim.

Gershon, Diane, Technology Feature: DNA Microarrays—More than than gene expression, It's a Small World, Microassays Move Downstream & On the Hardware Front, Nature, Oct. 20, 2005, pp. 1195-1198, vol. 437, Nature Publishing Group, USA.

Goluch, E.D. et al., A bio-barcode assay for on-chip attomolar-sensitivity protein detection, Lab on a Chip, Aug. 15, 2006, pp. 1293-1299, vol. 6, The Royal Society of Chemistry.

Grumann, M. et al, Parallelization of Chip-Based Fluorescence Immuno-Assays with Quantum-Dot Labelled Beads, The 13th International Conference on Solid-State Sensors, Actuators and Microsystems, Jun. 2005, pp. 1114-1117, IEEE.

Han, Mingyong et al., Quantum-dot-tagged microbeads for multiplexed optical coding of biomolecules, Nature Biotechnology, Jul. 2001, pp. 631-635, vol. 19, Nature Publishing Group, USA.

Hines, Margaret A. et al., Synthesis and Characterization of Strongly Luminescing ZnS-Capped CdSe Nanocrystals, Journal of Physical Chemistry B, 1996, pp. 468-471, vol. 100, No. 2, American Chemical Society, USA.

(56) References Cited

OTHER PUBLICATIONS

Kloepfer, Jeremiah A. et al., Photophysical Properties of Biologically Compatible CdSe Quantum Dot Structures, Journal of Physical Chemistry B, 2005, pp. 9996-10003, vol. 109, No. 20, American Chemical Society, USA.

Klostranec, Jesse M. et al., Convergence of Quantum Dot Barcodes with Microfluidics and Signal Processing for Multiplexed High-Throughput Infectious Disease Diagnostics, Nano Letters, Aug. 18, 2007, pp. 2812-2818, vol. 7, No. 9, American Chemical Society, USA.

Klostranec, Jesse M. et al., Quantum Dots in Biological and Biomedical Research: Recent Progress and Present Challenges, Advanced Materials, Aug. 4, 2006, pp. 1953-1964, vol. 18, No. 15, Wiley-VCH Verlag GmbH & Co. KGaA, Weinheim.

Li, Yougen et al., Multiplexed detection of pathogen DNA with DNA-based fluorescence nanobarcodes, Nature Biotechnology, Jul. 2005, pp. 885-889, vol. 23, No. 7, Nature Publishing Group, USA.

Liu, Wen-Tso et al., Microfluidic device as a new platform for immunofluorescent detection of viruses, Lab on a Chip, Oct. 4, 2005, pp. 1327-1330, vol. 5, The Royal Society of Chemistry.

Malamud, D. et al., Point Detection of Pathogens in Oral Samples, Adv Dent Res, Jun. 2005, pp. 12-16, vol. 18.

Marti et al., Design and characterization of two-dye and three-dye binary fluorescent probes for mRNA detection, Tetrahedron, Mar. 21, 2007, pp. 3591-3600, vol. 63, No. 17, Elsevier Science Publishers, Amsterdam, NL.

Mattoussi, H. et al., Luminescent Quantum Dot-Bioconjugates in Immunoassays, FRET, Biosensing, and Imaging Applications, JALA—Journal of the Association for Laboratory Automation, Feb. 2004, pp. 28-32, vol. 9, No. 1, The Association for Laboratory Automation, USA.

Medintz, Igor L. et al., Quantum dot bioconjugates for imaging, labelling and sensing, Nature Materials, Jun. 2005, pp. 435-446, vol. 4, Nature Publishing Group, USA.

Moré, Jorge J. et al., Computing a Trust Region Step, SIAM J. Sci. Stat. Comput., Sep. 1983, pp. 553-572, vol. 4, No. 3, Society for Industrial and Applied Mathematics.

Murray, C.B. et al., Synthesis and Characterization of Nearly Monodisperse CdE (E = S, Se, Te) Semiconductor Nanocrystallites, Journal of the American Chemical Society, 1993, pp. 8706-8715, vol. 115, No. 19, American Chemical Society, USA.

Neogi, A. et al., Enhanced luminescence efficiency from hydrogel microbead encapsulated quantum dots, Materials Research Society Symposium Proceedings, Jan. 1, 2007, pp. 202-207, vol. 959, Materials Research Society, USA.

Peng, Xiaogang et al., Epitaxial Growth of Highly Luminescent CdSe/CdS Core/Shell Nanocrystals with Photostability and Electronic Accessibility, Journal of the American Chemical Society, 1997, pp. 7019-7029, vol. 119, No. 30, American Chemical Society, USA.

Pregibon, Daniel C. et al., Multifunctional Encoded Particles for High-Throughput Biomolecule Analysis, Science, Mar. 9, 2007, pp. 1393-1396, vol. 315, American Association for the Advancement of Science, USA [downloaded on Mar. 9, 2009 from http://www.sciencemag.org].

Sathe, Tushar R. et al., Mesoporous Silica Beads Embedded With Semiconductor Quantum Dots and Iron Oxide Nanocrystals: Dual-Function Microcarriers for Optical Encoding and Magnetic Separation, Analytical Chemistry, Jul. 20, 2006, pp. 5627-5632, vol. 78, No. 16, American Chemical Society, USA.

Service, Robert F., DNA Analysis: Microchip Arrays Put DNA on The Spot, Science, Oct. 16, 1998, pp. 396-399, vol. 282, No. 5388, American Association for the Advancement of Science, USA [downloaded on Mar. 20, 2008 from http://www.sciencemag.org/cgi/content/full/282/5388/396].

Stavis, Samuel M. et al., Single molecule studies of quantum dot conjugates in a submicrometer fuidic channel, Lab on a Chip, Jan. 13, 2005, pp. 337-343, vol. 5, The Royal Society of Chemistry.

Sukhanova, A. et al., Nanocrystal-encoded fluorescent microbeads for proteomics: Antibody profiling and diagnostics of autoimmune diseases, Nano Letters, Aug. 2007, pp. 2322-2327, vol. 7, No. 8, American Chemical Society, USA.

Thomson, B. et al, Dispersion Copolymerization of Styrene and Divinylbenzee. II. Effect of Crosslinker on Particle Morphology, Journal of Applied Polymer Science, 1996, pp. 2009-2028, vol. 59, John Wiley & Sons, Inc.

Xu, Hongxia et al., Muliplexed SNP genotyping using the Qbeadn™ system: a quantum dot-encoded microsphere-based assay, Nucleic Acids Research, 2003, pp. 1-10, vol. 31, No. 8, Oxford University Press.

Xuan, Xiangchun et al., Focused electrophoretic motion and selected electrokinetic dispensing of particles of particles and cells in cross-microchannels, Electrophoresis, 2005, pp. 3552-3560, vol. 26, Wiley-VCH Verlag GmbH & co. KGaA, Weinheim.

Yun, Kwang-Seok et al., A microfluidic chip for measurement of biomolecules using a microbead-based quantum dot fluorescence assay, Measurement Science and Technology, 2006, pp. 3178-3183, vol. 17, IOP Publishing Ltd, UK.

Zaytseva, Natalya V. et al., Development of a microfluidic biosensor module for pathogen detection, Lab on a Chip, Jul. 6, 2005, pp. 805-811, vol. 5, The Royal Society of Chemistry.

\* cited by examiner

SYSTEMS AND METHODS FOR ENHANCING FLUORESCENT DETECTION OF TARGET MOLECULES IN A TEST SAMPLE

This application is a entry of PCT application no. PCT/CA08/01264, filed on Jul. 9, 2008, which claims the benefit of provisional application Ser. No. 60/948,643, filed on Jul. 9, 2007.

FIELD OF THE INVENTION

The present invention relates generally to the field of fluorescent detection, and more particularly, to systems and methods for enhancing fluorescent detection of target molecules in a test sample.

BACKGROUND OF THE INVENTION

Biomolecular assays may typically have required a readout signal to determine the success or failure of the experiment. Typically, for example, in prior art biomolecular sandwich assays, the analytes or target molecules to be detected may have been bound between biorecognition molecules (BRMs) and marker molecules. In the past, a positive result (and thus detection of the presence of the target molecule) may have been determined by detection of the readout signal, which in some cases may have been a fluorescent signal. The fluorescent signal may heretofore have been produced by excitation of a fluorophore bound to the marker molecule, such that the fluorophore emitted photons in the visible spectrum (i.e., as the fluorescent signal).

Exemplary prior art biomolecular sandwich assays may have included genomic assays, where the BRMs may have been single-stranded DNA immobilized on the surface of a substrate (e.g., a microbead). Similarly, the marker molecules may have included single-stranded marker DNA bound to one or more fluorophores. In operation, such prior art genomic assays may have involved a first hybridization reaction between the BRMs and the target molecules, if present. (The target molecules may have included single-stranded target DNA of interest in the experiment.) Thereafter, such prior art genomic assays may have involved a second hybridization reaction between the marker molecules and the target molecules, if present.

Other exemplary prior art biomolecular sandwich assays may have included immunoassays, where the BRMs may heretofore have been first antibody molecules immobilized on a substrate. Similarly, the marker molecules may heretofore have been second antibody molecules (alternately, "marker antibodies") bound to one or more fluorophores. In operation, such prior art immunoassays may have involved a first reaction between the BRMs and the target molecules, if present. (The target molecules may have included target antigen molecules, or analytes, of interest in the experiment.) Thereafter, such prior art immunoassays may have involved a second reaction between the marker antibodies and the target antigen molecules, if present.

In the past, it may generally have been thought that molecular fluorophores can provide useful and/or sensitive methods for the detection of binding events in biomolecular assays. Such molecular fluorophores may heretofore have been used, when bound, to provide a fluorescent readout signal. It may generally have been thought that suitable molecular fluorophores might include, for example, fluorescein, rhodamine dyes, or ALEXA FLUOR® series dyes (such as those manufactured by Molecular Probes, Inc. of Eugene, Oreg.). More recently, quantum dots (QDs) may have been considered for potential uses as fluorophores.

It may heretofore have been generally thought that assay sensitivity, and the ability to detect fluorescent readout signals, depends on an ability to observe an emission from a chosen marker fluorophore. Accordingly, much assay sensitivity research to date may have been largely aimed at increasing the ability to observe emissions from chosen marker fluorophores. Related developments may heretofore have, therefore, included highly sensitive photomultiplier tubes, more efficient photon collection optics, and/or the use of microfluidic systems. One or more of these developments may have sought to maximize detection sensitivity for very low fluxes of photons, possibly as might be emitted from a small area in a microarray or microbead biomolecular assay.

It may now be believed (though it is not essential to the working of the present invention) that the sensitivity in detecting fluorescent readout signals, and indeed assay sensitivity as a whole, may also depend upon an ability to excite the chosen marker fluorophores. Assay detection sensitivity may, therefore, yet be improved by improving the ability to excite the chosen marker fluorophores. Accordingly, it may be desirable to provide an improved method and system for local excitation of specific fluorophores.

It may be thought, though it may not be essential to the working of the present invention, that fluorescent molecules or QDs enter an electronically "excited state" before they are capable of emitting one or more detectable photons in the visible spectrum. It is also believed, though it is not essential to the working of the present invention, higher percentages of excited molecules in a population may lead to a higher absolute number of (detectable) photons being emitted. Although not necessary to the working of the present invention, it may be thought that an increase in the total number of electronically excited fluorophore molecules may directly increase the assay's detection sensitivity to that population of molecules.

Various techniques may heretofore have been used to produce molecular excitation, including the use of thermal energy (heat), electrical stimulation, and/or light absorption. When an emission of a fluorescent signal is the desired effect, the use of light absorption may be a particularly efficient method for exciting molecular fluorophores.

Previously, lasers may have been used to excite fluorophores. Lasers can be relatively intense sources of light and may, therefore, be efficient at exciting molecular dyes. Lasers may, however, emit very narrow bandwidths of visible light, having a specific single polarization. As such, lasers may not be as efficient at exciting random orientations of molecular fluorophores as might be desired.

Now, in biomolecular sandwich assays, it may be advantageous for both the microbeads and the marker molecules to emit fluorescent readout signals in a test positive scenario. In such a contemplated situation, multiple wavelengths of incident light might heretofore have been required to adequately excite both the microbead fluorophores and the marker fluorophores.

Accordingly, there may be a need to provide an improved ability to excite bound fluorophores, and/or to provide for increased numbers of excited bound fluorophores.

There may also be a need to provide an improved ability to excite fluorophores, and/or to provide for increased numbers of excited fluorophores, bound at various orientations.

There may also be a need to provide for an enhanced emission from fluorophores by controllable localized excitation.

It is an object of a preferred embodiment according to the present invention to provide a system and/or method for enhancing fluorescent detection of target molecules.

It is an object of one preferred embodiment according to the present invention to provide a system and/or method for enhancing fluorescent detection of target molecules in a microbead assay.

It is an object of a preferred embodiment according to the present invention to provide a system and/or method which excites the BRM or marker fluorophores (preferably, the marker fluorophores) via a fluorescent signal emitted from the other (preferably, from the BRM fluorophores).

It is also an object of one preferred embodiment according to the present invention to provide a system and/or method which advantageously tailors an emission profile and/or an intensity of one or more QDs to provide for, and/or control, localized excitation of one or more other immobilized fluorophores in the assay.

It is an object of the present invention to obviate or mitigate one or more of the aforementioned disadvantages associated with the prior art, and/or to achieve one or more of the aforementioned objects of the invention.

SUMMARY OF THE INVENTION

According to the invention, there is disclosed a method of enhancing fluorescent detection of target molecules in a test sample. The method is for use with an irradiating device. The method includes a step of (a) providing one or more first fluorophores operatively adapted for absorption of electromagnetic frequency (EMF) radiation, and for emission of a first fluorescent signal following absorption of the EMF radiation. The method also includes a step of (b) providing one or more second fluorophores operatively adapted for absorption of a first incident portion of the first fluorescent signal, and for emission of a second fluorescent signal following absorption of the first incident portion. The second fluorescent signal is distinguishable from the first fluorescent signal. The first fluorophores and the second fluorophores are adapted for operative combination with the test sample, and for securement relative to the target molecules, if present in the test sample, so as to secure the first fluorophores relative to the second fluorophores. Following operative irradiation of at least the first fluorophores with the EMF radiation via the irradiating device, the first fluorophores emit the first fluorescent signal. If the target molecules are present in the test sample, the second fluorophores absorb the first incident portion of the first fluorescent signal and emit the second fluorescent signal. Thus, the first spectral signal is operatively detectable, together with the second spectral signal if the target molecules are present in the test sample.

According to an aspect of one preferred embodiment of the invention, in step (a), the first fluorophores may preferably, but need not necessarily, be characterized by a first fluorophore emission profile, preferably corresponding to the first fluorescent signal. Preferably in step (b), the second fluorophores may preferably, but need not necessarily, be characterized by a second fluorophore absorption profile which preferably substantially overlaps with the first fluorophore emission profile.

According to an aspect of one preferred embodiment of the invention, preferably in step (a), the first fluorophore emission profile may preferably, but need not necessarily, be characterized by a peak intensity at a wavelength of about 580 nanometers (nm).

According to an aspect of one preferred embodiment of the invention, preferably in step (a), the first fluorophores may preferably, but need not necessarily, be characterized by a first fluorophore absorption profile, preferably substantially corresponding to the EMF radiation. Preferably in step (b), the second fluorophores may preferably, but need not necessarily, be characterized by a second fluorophore emission profile, preferably corresponding to the second fluorescent signal, which may preferably be substantially removed from the first fluorophore absorption profile.

According to an aspect of one preferred embodiment of the invention, preferably in step (a), the first fluorophores may preferably, but need not necessarily, be bound by microbeads. Preferably, the method may preferably also include step (c), preferably after step (a), of providing biorecognition molecules (BRMs) adapted to operatively bind with the microbeads and/or the target molecules, preferably so as to secure the first fluorophores relative to the target molecules if present in the test sample.

According to an aspect of one preferred embodiment of the invention, preferably in step (c), the BRMs may preferably, but need not necessarily, include one or more antibody molecules.

According to an aspect of one preferred embodiment of the invention, the method may preferably, but need not necessarily, be for detection of one or more single-stranded target DNA molecules as the target molecules. Preferably in step (c), the BRMs may preferably, but need not necessarily, include one or more single-stranded biorecognition DNA molecules complementary to, and/or adapted to operatively hybridize with, the target DNA molecules.

According to an aspect of one preferred embodiment of the invention, preferably in step (a), the first fluorophores may preferably, but need not necessarily, include quantum dots of one or more quantum dot types.

According to an aspect of one preferred embodiment of the invention, preferably in step (a), the intensity of the first spectral signal may preferably, but need not necessarily, be dependent upon the number of the quantum dots bound by each of the microbeads.

According to an aspect of one preferred embodiment of the invention, preferably in step (a), the color of the first spectral signal may preferably, but need not necessarily, be dependent upon the size of the quantum dot types bound by each of the microbeads.

According to an aspect of one preferred embodiment of the invention, preferably in step (b), the second fluorophores may preferably, but need not necessarily, be adapted for substantially direct operative binding with the target molecules.

According to an aspect of one preferred embodiment of the invention, the method may preferably also include step (d), preferably after step (b), of providing marker molecules adapted to operatively bind with the second fluorophores and/or the target molecules, preferably so as to secure the second fluorophores relative to the target molecules if present in the test sample.

According to an aspect of one preferred embodiment of the invention, preferably in step (d), the marker molecules may preferably, but need not necessarily, include one or more antigen molecules.

According to an aspect of one preferred embodiment of the invention, the method may preferably, but need not necessarily, be for detection of one or more single-stranded target DNA molecules as the target molecules. Preferably in step (d), the marker molecules may preferably, but need not necessarily, include one or more single-stranded marker DNA molecules complementary to, and/or adapted to operatively hybridize with, the target DNA molecules.

According to an aspect of one preferred embodiment of the invention, the method may preferably, but need not necessarily, be for use with a laser as the irradiating device. Preferably in step (a), the EMF radiation may preferably, but need not necessarily, have a wavelength of about 488 nanometers (nm).

According to an aspect of one preferred embodiment of the invention, preferably following operative combination of the first fluorophores and/or the second fluorophores with the test sample, the target molecules, if present in the test sample, may preferably secure the second fluorophores within a predetermined maximum range of the first fluorophores. A radiative flux of the first spectral signal may preferably, but need not necessarily, be substantially unabated over the predetermined maximum range.

According to an aspect of one preferred embodiment of the invention, the predetermined maximum range may preferably, but need not necessarily, be dependent upon the first fluorophores, preferably as provided in step (a). The predetermined maximum range may preferably, but need not necessarily, be less than about 10 micrometers ($\mu$m).

According to an aspect of one preferred embodiment of the invention, preferably in step (b), the second fluorophores may also preferably, but not necessarily, be operatively adapted for absorption of the EMF radiation, and/or for emission of the second fluorescent signal following absorption of the EMF radiation.

According to an aspect of one preferred embodiment of the invention, the method may preferably, but need not necessarily, also include step (e), preferably after step (b), of operatively combining the first fluorophores with the test sample and/or the second fluorophores.

According to an alternate aspect of one preferred embodiment of the invention, the method may preferably, but need not necessarily, include alternate step (e), preferably after step (c), of operatively combining the microbeads with the BRMs, the test sample, and/or the second fluorophores.

According to another alternate aspect of one preferred embodiment of the invention, the method may preferably, but need not necessarily, include another alternate step (e), preferably after step (d), of operatively combining the first fluorophores with the test sample, the marker molecules, and/or the second fluorophores.

According to an aspect of one preferred embodiment of the invention, the method may preferably, but need not necessarily, also include step (f), preferably after step (e), of operatively irradiating at least the first fluorophores with the EMF radiation, preferably via the irradiating device.

According to an aspect of one preferred embodiment of the invention, preferably in step (b), the second fluorophores may also preferably, but not necessarily, be operatively adapted for absorption of the EMF radiation, and/or for emission of the second fluorescent signal following absorption of the EMF radiation. According to this aspect of the invention, the method may preferably, but need not necessarily, also include alternate step (f), preferably after step (e), of operatively irradiating the first fluorophores and/or the second fluorophores with the EMF radiation, preferably via the irradiating device.

According to an aspect of one preferred embodiment of the invention, the method may preferably, but need not necessarily, also include step (g), preferably after step (f), of operatively detecting the first spectral signal, preferably together with the second spectral signal if the target molecules are present in the test sample.

According to the invention, there is also disclosed a system for enhancing fluorescent detection of target molecules in a test sample. The system is for use with an irradiating device. The system includes one or more first fluorophores operatively adapted for absorption of electromagnetic frequency (EMF) radiation, and for emission of a first fluorescent signal following absorption of the EMF radiation. The system also includes one or more second fluorophores operatively adapted for absorption of a first incident portion of the first fluorescent signal, and for emission of a second fluorescent signal following absorption of the first incident portion. The second fluorescent signal is distinguishable from the first fluorescent signal. The first fluorophores and the second fluorophores are adapted for operative combination with the test sample, and for securement relative to the target molecules, if present in the test sample, so as to secure the first fluorophores relative to the second fluorophores. Following operative irradiation of at least the first fluorophores with the EMF radiation via the irradiating device, the first fluorophores emit the first fluorescent signal and, if the target molecules are present in the test sample, the second fluorophores absorb the first incident portion of the first fluorescent signal and emit the second fluorescent signal. Thus, the first spectral signal is operatively detectable, together with the second spectral signal if the target molecules are present in the test sample.

According to an aspect of one preferred embodiment of the invention, the first fluorophores may preferably, but need not necessarily, be characterized by a first fluorophore emission profile, preferably corresponding to the first fluorescent signal. The second fluorophores may preferably, but need not necessarily, be characterized by a second fluorophore absorption profile which may preferably substantially overlap with the first fluorophore emission profile.

According to an aspect of one preferred embodiment of the invention, the first fluorophore emission profile may preferably, but need not necessarily, be characterized by a peak intensity at a wavelength of about 580 nanometers (nm).

According to an aspect of one preferred embodiment of the invention, the first fluorophores may preferably, but need not necessarily, be characterized by a first fluorophore absorption profile, preferably substantially corresponding to the EMF radiation. The second fluorophores may preferably, but need not necessarily, be characterized by a second fluorophore emission profile, preferably corresponding to the second fluorescent signal, which may preferably be substantially removed from the first fluorophore absorption profile.

According to an aspect of one preferred embodiment of the invention, the first fluorophores may preferably, but need not necessarily, be bound by microbeads. The system may preferably, but need not necessarily, also include biorecognition molecules (BRMs) adapted to operatively bind with the microbeads and/or the target molecules, preferably so as to secure the first fluorophores relative to the target molecules if present in the test sample.

According to an aspect of one preferred embodiment of the invention, the BRMs may preferably, but need not necessarily, include one or more antibody molecules.

According to an aspect of one preferred embodiment of the invention, the system may preferably, but need not necessarily, be for detection of one or more single-stranded target DNA molecules as the target molecules. The BRMs may preferably, but need not necessarily, include one or more single-stranded biorecognition DNA molecules complementary to, and/or adapted to operatively hybridize with, the target DNA molecules.

According to an aspect of one preferred embodiment of the invention, the first fluorophores may preferably, but need not necessarily, include quantum dots of one or more quantum dot types.

According to an aspect of one preferred embodiment of the invention, the intensity of the first spectral signal may preferably, but need not necessarily, be dependent upon the number of the quantum dots bound by each of the microbeads.

According to an aspect of one preferred embodiment of the invention, the color of the first spectral signal may preferably, but need not necessarily, be dependent upon the size of the quantum dot types bound by each of the microbeads.

According to an aspect of one preferred embodiment of the invention, the second fluorophores may preferably, but need not necessarily, be adapted for substantially direct operative binding with the target molecules.

According to an aspect of one preferred embodiment of the invention, the system may preferably, but need not necessarily, also include marker molecules adapted to operatively bind with the second fluorophores and/or the target molecules, preferably so as to secure the second fluorophores relative to the target molecules if present in the test sample.

According to an aspect of one preferred embodiment of the invention, the marker molecules may preferably, but need not necessarily, include one or more antigen molecules.

According to an aspect of one preferred embodiment of the invention, the system may preferably, but need not necessarily, be for detection of one or more single-stranded target DNA molecules as the target molecules. The marker molecules may preferably, but need not necessarily, include one or more single-stranded marker DNA molecules complementary to, and/or adapted to operatively hybridize with, the target DNA molecules.

According to an aspect of one preferred embodiment of the invention, the second fluorophores may preferably, but need not necessarily, be adapted to be operatively secured substantially adjacent to distal end portions of the marker DNA molecules.

According to an aspect of one preferred embodiment of the invention, the second fluorophores may preferably, but need not necessarily, include one or more fluorescent dyes.

According to an aspect of one preferred embodiment of the invention, the fluorescent dyes may preferably, but need not necessarily, include Cyanine-5 (Cy5) molecular dyes.

According to an aspect of one preferred embodiment of the invention, the first fluorophores may preferably, but need not necessarily, have a higher emission wavelength than the second fluorophores.

According to an aspect of one preferred embodiment of the invention, the system may preferably, but need not necessarily, be for use with a laser as the irradiating device. The EMF radiation may preferably, but need not necessarily, have a wavelength of about 488 nanometers (nm).

According to an aspect of one preferred embodiment of the invention, preferably following operative combination of the first fluorophores and/or the second fluorophores with the test sample, the target molecules, if present in the test sample, may preferably secure the second fluorophores within a predetermined maximum range of the first fluorophores. A radiative flux of the first spectral signal may preferably, but need not necessarily, be substantially unabated over the predetermined maximum range.

According to an aspect of one preferred embodiment of the invention, the predetermined maximum range may preferably, but need not necessarily, be dependent upon the first fluorophores. The predetermined maximum range may preferably, but need not necessarily, be less than about 10 micrometers (μm).

According to an aspect of one preferred embodiment of the invention, the predetermined maximum range may preferably, but need not necessarily, be in the order of about 300 nanometers (nm).

According to an aspect of one preferred embodiment of the invention, the method and/or system may preferably, but need not necessarily, be for detection of infectious diseases.

According to an aspect of one preferred embodiment of the invention, the method and/or system may preferably, but need not necessarily, be for detection of cancer.

According to an aspect of one preferred embodiment of the invention, the method and/or system may preferably, but need not necessarily, be for detection of cystic fibrosis.

According to an aspect of one preferred embodiment of the invention, the method and/or system may preferably, but need not necessarily, be for use in a biomolecular assay.

According to an aspect of one preferred embodiment of the invention, the method and/or system may preferably, but need not necessarily, be for use in a sandwich assay as the biomolecular assay.

According to an aspect of one preferred embodiment of the invention, the second fluorophores also may preferably, but need not necessarily, be operatively adapted for absorption of the EMF radiation, and/or for emission of the second fluorescent signal following absorption of the EMF radiation.

According to an aspect of one preferred embodiment of the invention, the microbeads may preferably, but need not necessarily, be operatively combined with the BRMs, the test sample, and/or the second fluorophores.

According to an aspect of one preferred embodiment of the invention, the first fluorophores may preferably, but need not necessarily, be operatively combined with the test sample, the marker molecules, and/or the second fluorophores.

According to an aspect of one preferred embodiment of the invention, the second fluorophores also may preferably, but need not necessarily, be operatively adapted for absorption of the EMF radiation, and/or for emission of the second fluorescent signal following absorption of the EMF radiation. The first fluorophores and/or the second fluorophores may preferably, but need not necessarily, be operatively irradiated with the EMF radiation, preferably via the irradiating device.

According to the invention, there is additionally disclosed a fluorophore, quantum dot and/or fluorescent dye for use as one of the first or second fluorophores in the method and/or system described above.

According to the invention, there are additionally disclosed microbeads, biorecognition molecules, and/or marker molecules for use in the method and/or system described above.

Other advantages, features and/or characteristics of the present invention, as well as methods of operation and/or functions of the related elements of the method and system, and/or the combination of steps, parts and/or economies of manufacture, will become more apparent upon consideration of the following detailed description and the appended claims with reference to the accompanying drawings, the latter of which are briefly described hereinbelow.

BRIEF DESCRIPTION OF THE DRAWINGS

The novel features which are believed to be characteristic of the system and method according to the present invention, as to their structure, organization, use, and/or method of operation, together with further objectives and/or advantages thereof, may be better understood from the following drawings in which presently preferred embodiments of the invention will now be illustrated by way of example. It is expressly understood, however, that the drawings are for the purpose of

Figure 1:
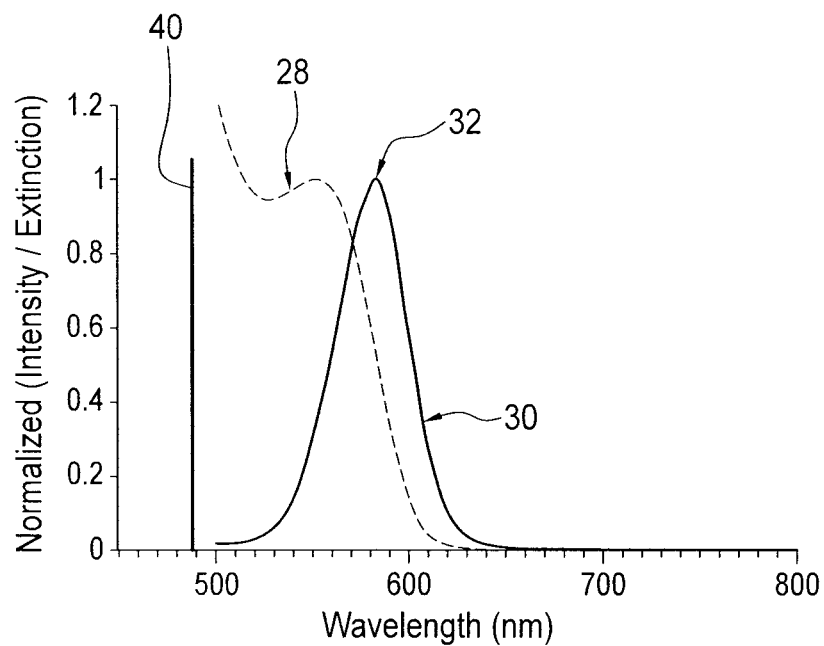
Figure 2:
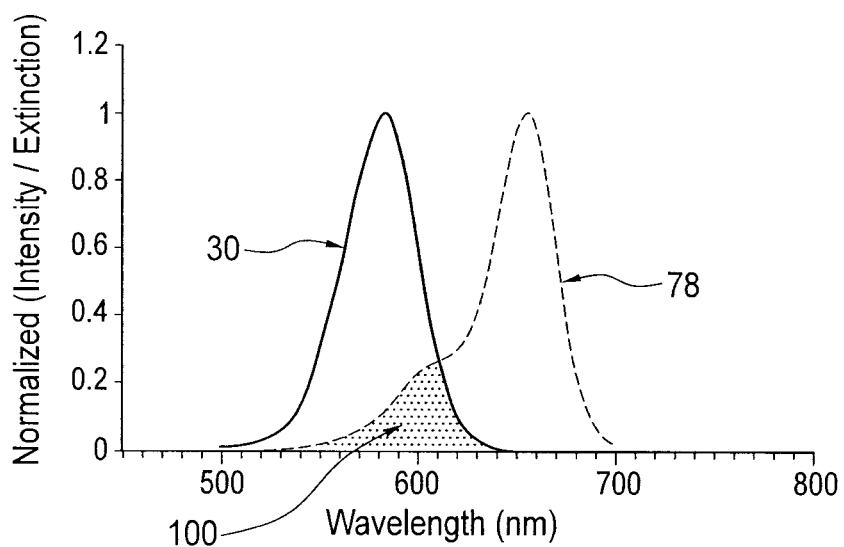
Figure 3:
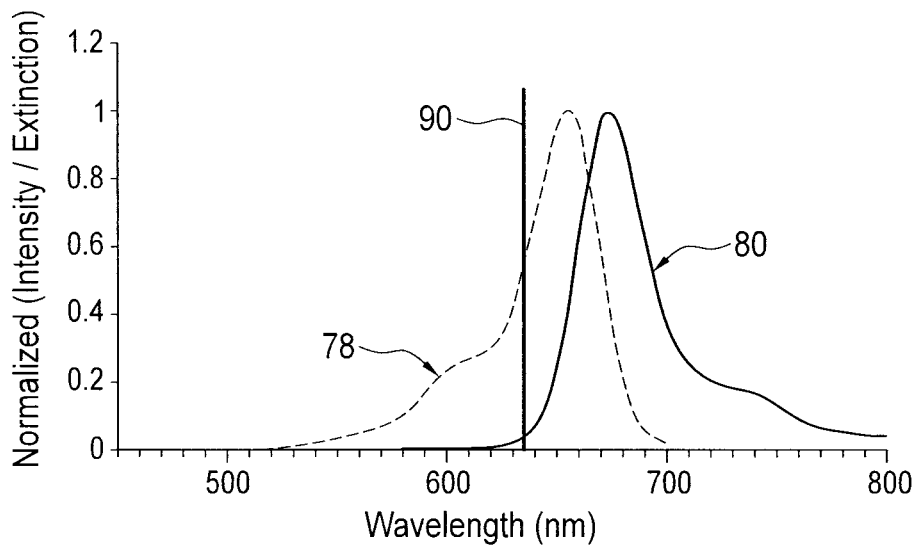
Figure 4:
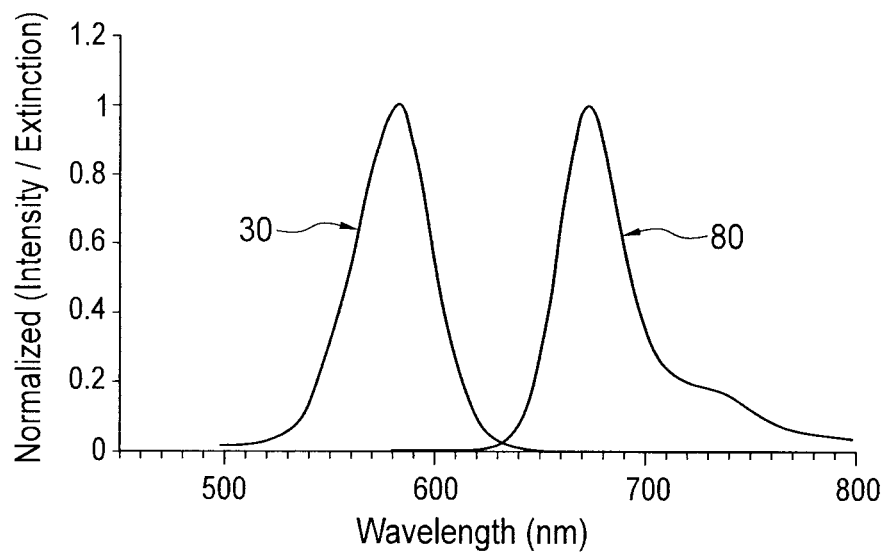
Figure 5:
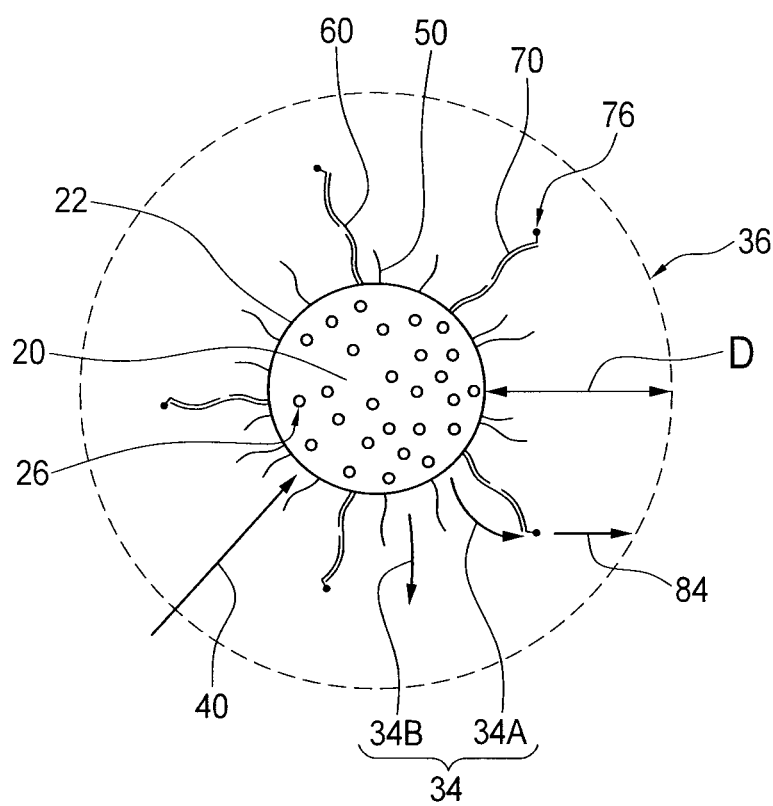
Figure 6:
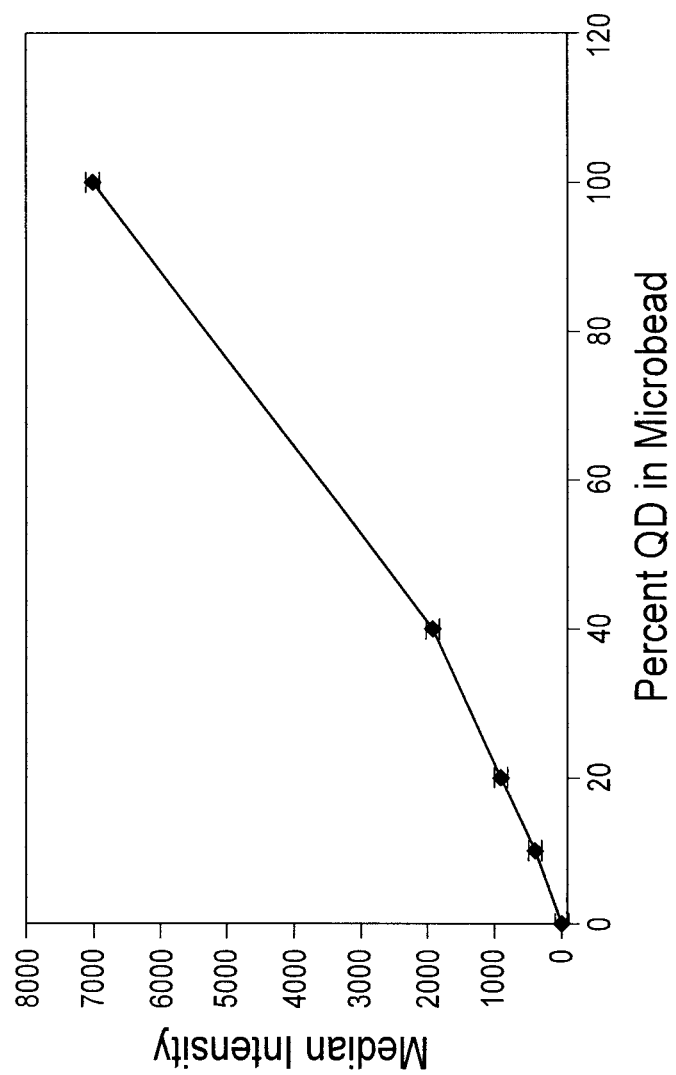
Figure 7A:
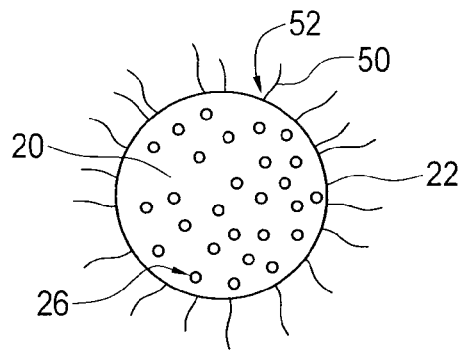
Figure 7B:
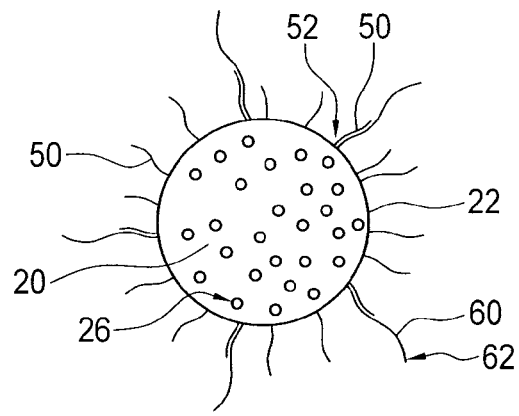
Figure 7C:
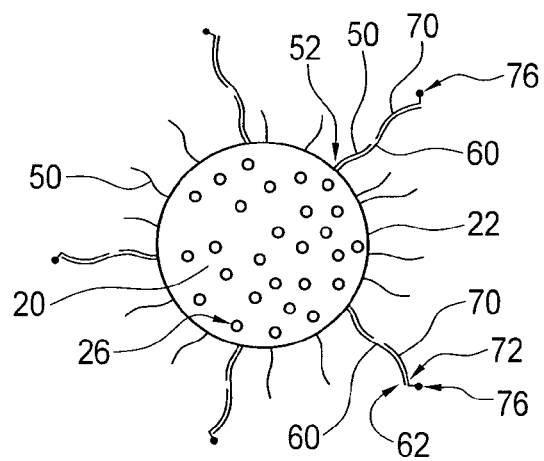
Figure 8:
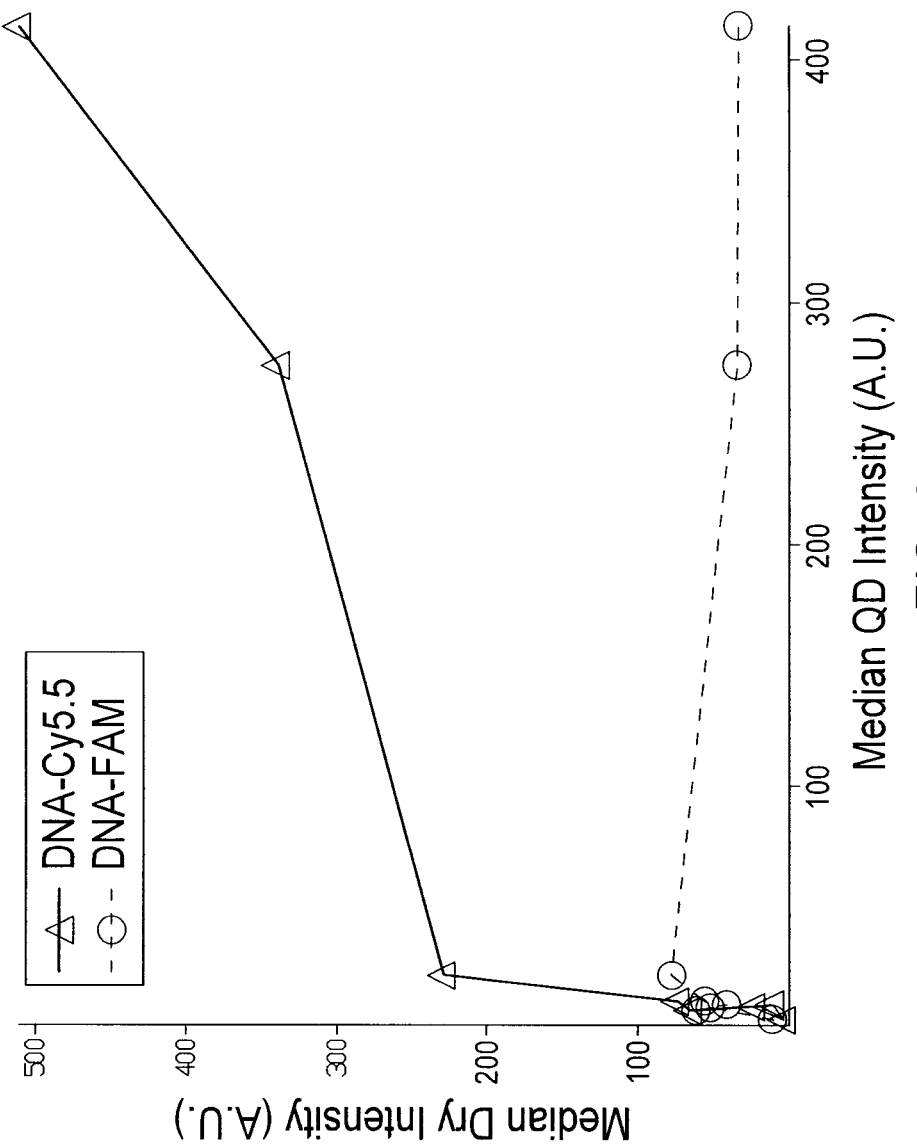
Figure 9:
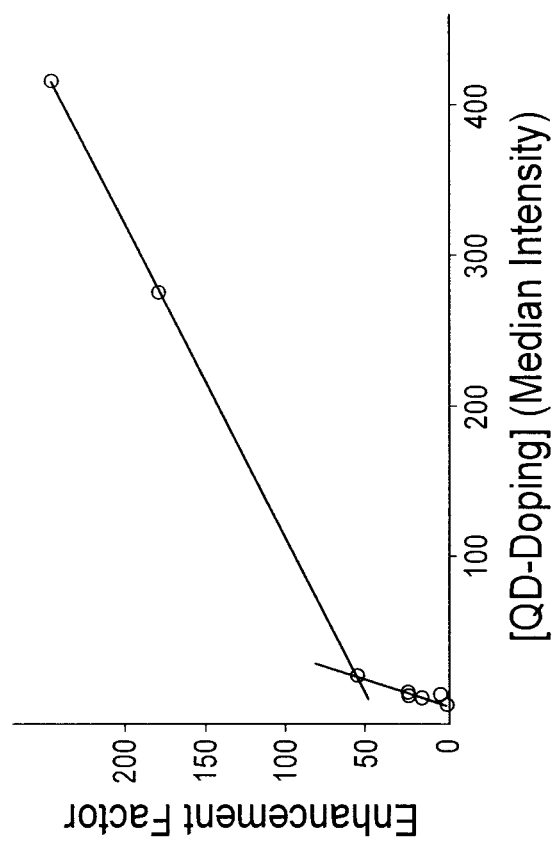
Figure 10:
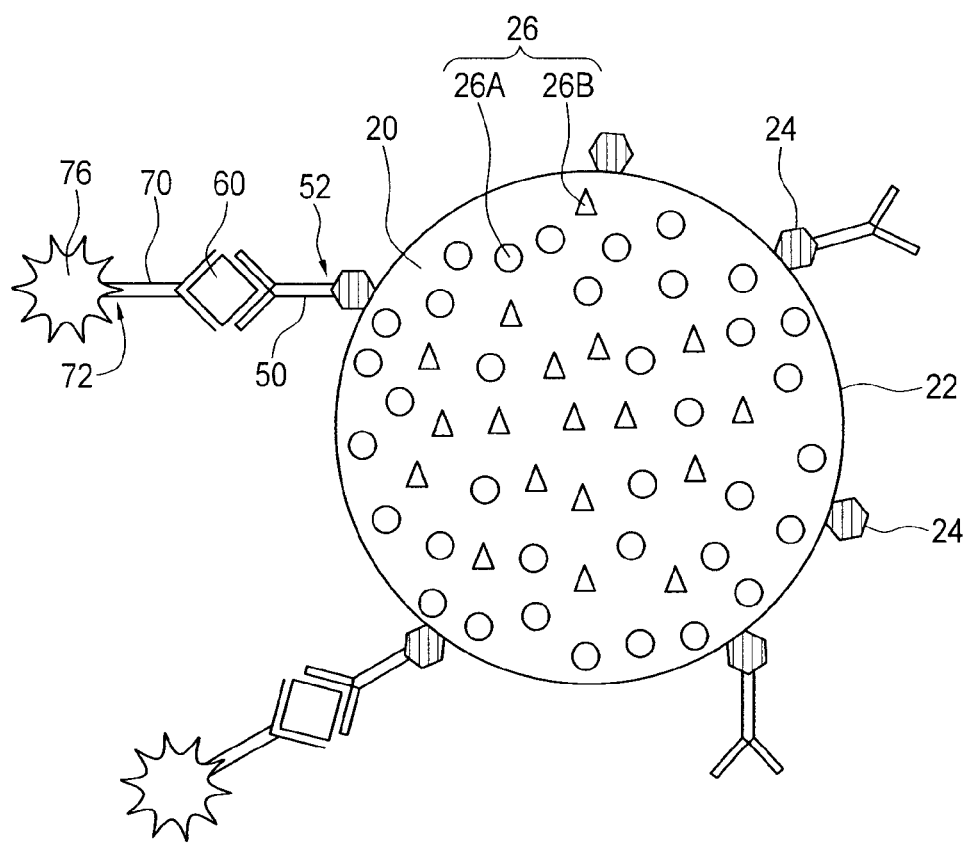

9 illustration and description only, and are not intended as a definition of the limits of the invention. In the accompanying drawings:

FIG. 1 is a graph of the absorption and emission profiles for a first fluorophore according to a preferred embodiment of the present invention;

FIG. 2 is a graph of the emission profile for the first fluorophore represented in FIG. 1, and the absorption profile for a second fluorophore according to the preferred embodiment of the present invention;

FIG. 3 is a graph of the absorption and emission profiles for the second fluorophore represented in FIG. 2;

FIG. 4 is a graph of the emission profiles for the first and second fluorophores represented in FIGS. 1 and 2, respectively;

FIG. 5 is an illustrative representation of a system including the first and second fluorophores, shown in conjunction with target molecules, according to the preferred embodiment of the present invention;

FIG. 6 is a graph of various first fluorophore doping percentages in microbeads against the first fluorescent signal intensity according to the preferred embodiment of the present invention;

FIG. 7A is an illustrative representation of the system of FIG. 5, shown without the target molecules, marker molecules and second fluorophores;

FIG. 7B is an illustrative representation of the system of FIG. 7A shown in conjunction with the target molecules;

FIG. 7C is an illustrative representation of the system of FIG. 7B, shown in conjunction with the marker molecules and the second fluorophores;

FIG. 8 is a graph of various first fluorescent signal intensities against the median second fluorescent signal intensity according to the preferred embodiment of the present invention, and showing a median fluorescent emission signal for a molecular FAM dye for comparison purposes;

FIG. 9 is a graph of various median first fluorescent signal intensities against the enhancement factor for the second fluorescent signal according to the preferred embodiment of the present invention; and FIG. 10 is an illustrative representation, similar to FIG. 5, of an alternate system including the first and second fluorophores, shown in conjunction with target molecules, according to an alternate preferred embodiment of the present invention.

DETAILED DESCRIPTION OF THE PREFERRED EMBODIMENTS

Referring now to FIGS. 1-10 of the drawings, there are represented methods and systems for fluorescent detection of target molecules 60 according to the present invention. The methods and systems according to the present invention are adapted to test for the presence of the target molecules 60 in a test sample (not shown).

Generally, and as best seen in FIGS. 5, 7C and 10, the system includes a microbead 20 and biorecognition molecules (BRMs) 50. Each microbead 20 contains first fluorophores 26. The BRMs 50 bind the target molecules 60 (if present in the test sample), which in turn are bound to marker molecules 70 bearing second fluorophores 76.

Use of the present invention in biomolecular assays may advantageously provide for an internal volume of the microbead 20 to be used as a localized compartment to hold numerous ones of the first fluorophores 26. Since, as may be described in considerably greater detail elsewhere herein, the first fluorophores 26 are preferably highly customizable quantum dots (QDs), each microbead 20 may contain thousands, or even millions, of the first fluorophores 26. Additionally, and as may also be described in considerably greater detail elsewhere herein, because the QDs may be tailored and/or customized to have various predetermined and/or selected emission energies, the first fluorophores 26 may be chosen and embedded within the microbead 20, such that the fluorescence emission properties of the first fluorophores 26 will preferably overlap only with another specific fluorophore.

As best seen in FIGS. 5, 7A and 10, the BRMs 50 are bound to a surface 22 of the microbead 20. More specifically, and as best seen in FIG. 10, proximal end portions 52 of the BRMs 50 (being those portions most closely situated towards the microbead 20) are preferably bound to functional groups 24 provided on the surface 22 of the microbead 20.

In one preferred embodiment according to the present invention, and as best seen in FIGS. 5 and 7A-7C, the BRMs 50 may be provided as one or more single-stranded biorecognition DNA (BRM-ssDNA) molecules. When the BRMs 50 are operatively bound to the microbead 20, they together form a microbead/BRM-ssDNA substrate (as best seen in FIG. 7A).

The microbead/BRM-ssDNA substrate may then preferably be added to a solution (e.g., a plasma/PCR product). Preferably, the microbead/BRM-ssDNA substrate will then diffuse through the solution, while searching for and/or scavenging, via hybridization, the target molecules 60.

In one preferred embodiment according to the present invention, and as best seen in FIG. 7B, the target molecules 60 may be one or more target strands of a nucleic acid sequence complementary to at least one of the BRM-ssDNA molecules. The target molecules 60 operatively bind with the BRMs 50 as shown in FIG. 7B, and have unbound distal end portions 62—preferably at least one each. The distal end portions 62 are those portions of the target molecules 60 which, in an operatively bound configuration (as shown in FIG. 7B), are furthest removed from the surface 22 of the microbead 20. When the target molecules 60 are operatively bound to the microbead/BRM-ssDNA substrate, they together form a microbead/BRM-ssDNA/target substrate (as best seen in FIG. 7B).

Subsequently, the marker molecules 70 are preferably added to the microbead/BRM/target substrate shown in FIG. 7B. A second hybridization reaction will preferably take place to form the test positive end product shown in FIG. 7C. The second fluorophores 76 are preferably operatively bound to distal end portions 72 of the marker molecules 70 (as best seen in FIG. 7C). The distal end portions 72 are those portions of the marker molecules 70 which, in an operatively bound configuration (as shown in FIG. 7C), are furthest removed from the surface 22 of the microbead 20. Preferably, the marker molecules 70 operatively bind to the distal end portions 62 of the target molecules 60 (as best seen in FIG. 7C).

In an alternate preferred embodiment, and as shown in FIG. 10, the BRMs 50 may be provided as one or more BRM antibody molecules, the target molecules 60 may be provided as one or more target antigen molecules, and the marker molecules 70 may be provided as one or more marker antibody molecules. The BRM antibody molecules and the marker antibody molecules are operatively bound to the target antigen molecules. The second fluorophores 76 are preferably operatively bound to distal end portions 72 of the marker antibodies.

Preferably, and as best seen in FIGS. 5, 7C and 10, when the target molecules 60 are present in the test sample (not shown), they operatively secure the first fluorophores 26 relative to the second fluorophores 76.

With further reference to FIG. 5, the first fluorophores 26 will be seen to operatively emit a first fluorescent signal 34 after absorption of electromagnetic frequency (EMF) radiation 40. The first fluorescent signal 34 preferably radiates outward from the surface 22 of the microbead 20.

As best seen in FIG. 5, a first incident portion 34A of the first fluorescent signal 34 is preferably incident upon one or more of the second fluorophores 76, and a second detectable portion 34B of the first fluorescent signal 34 radiates further outward from the microbead 20.

The second fluorophores 76 are adapted for operative absorption of the first incident portion 34A of the first fluorescent signal 34. After absorption of the first incident portion 34A, the second fluorophores 76 operatively emit a second fluorescent signal 84 (as shown in FIG. 5). As may be best appreciated from FIG. 4, and as may be described in considerably greater detail elsewhere herein, the second fluorescent signal 84 is preferably readily distinguishable from the first florescent signal 34.

As shown in FIGS. 5, 7C and 10, the target molecules 60 secure the first fluorophores 26 relative to the second fluorophores 76. As such, the first incident portion 34A of the first fluorescent signal 34 selectively excites the second fluorophore 76, and enhances emission of the second fluorescent signal 84, preferably only if the target molecules 60 are present in the test sample (not shown). Without intending to be bound by theory, the aforementioned effect is believed to occur only when the target molecules 60 are present in the test sample, since the target molecules 60 operatively secure the first fluorophores 26 and the second fluorophores 76 relative to each other. In this manner, the target molecules 60 enable greater absorption of the first fluorescent signal 34 by the second fluorophores 76. This selective excitation of the second fluorophores 76 by the first fluorophores 26 when the target molecules 60 are present in the test sample (not shown) is believed—again, without intending to be bound by theory—to impart sensitivity, and selectivity, to the assay because unbound second fluorophores 76 (or molecular dyes of other energies) may show little or no enhancement of their respective emission spectral signals.

More particularly, and as best seen in FIG. 5, the first fluorophores 26 will preferably emit photons (in the form of the first fluorescent signal 34) in all directions from the surface 22 of the microbead 20. In this manner, enhancement of the second fluorescent signal 84 is dependent upon the second fluorophores 76 being located within a predetermined maximum range (as indicated generally by dimension "D" in FIG. 5) from the first fluorophores 26. Where, as here, the first fluorophores 26 may be bound substantially at the surface 22 of the microbead 20, it may be possible to measure the predetermined maximum range "D" from the surface 22 of the microbead 20. The predetermined maximum range "D" defines a region 36 of substantially unabated radiative flux (or high photon flux) for the first fluorescent signal 34. In this region 36, similar photon densities (e.g., within 10%) may be observed at the surface 22 of the microbead 20 and at the predetermined maximum range "D" from the surface 22. Without intending to be bound by theory, it is believed that the efficiency of the assay is negligibly diminished when the second fluorophores 76 are bound within the predetermined maximum range "D" from the surface 22 of the microbead 20. Although not essential to the working of the present invention, it may be generally believed that, according to one preferred embodiment and by way of non-limiting example only, when the microbead 20 is provided with a diameter of about five micrometers (5 µm), the predetermined maximum range "D" may be in the approximate order of about 300 nanometers (nm).

In one preferred embodiment, and as best seen in FIGS. 5 and 7A-7C, the first fluorophores 26 embedded within the microbead 20 may be provided in the form of QDs adapted to emit photons centered at about 580 nanometers (nm)—i.e., generally in the yellow range of the visible light spectrum. These QDs may serve as a source of excitation energy for the second fluorophores 76, which preferably may be provided in the form of a Cyanine-5 (Cy5) molecular dye—more preferably, a Cyanine-5.5 (Cy5.5) molecular dye—that absorbs yellow light strongly and emits photons having a wavelength generally situated towards the red end of the visible light spectrum.

As may be appreciated from a consideration of FIG. 3, when the second fluorophores 76 are provided in the form of the Cy5 molecular dye, they may be excited, inter alia, by incident radiation 90 (e.g., coherent light from a laser) having a wavelength of about 635 nanometers (nm)—i.e., provided that the incident coherent radiation 90 lies within a second fluorophore absorption profile 78 (as best seen in FIG. 3) characteristic of the Cy5 molecular dye. Thereafter, the CY5 molecular dye is adapted to operatively emit the second fluorescent signal 84. The second fluorescent signal 84 corresponds to a second fluorophore emission profile 80 (best seen in FIG. 3) characteristic of the Cy5 molecular dye. Although not essential to the working of the present invention, the intensity of the second fluorescent signal 84 emitted by the Cy5 molecular dye may depend generally upon the amount of the incident radiation 90 absorbed thereby.

Although not necessary to the operation of the invention, in one preferred embodiment, the region 36 of substantially unabated radiative flux (best seen in FIG. 5) may be dependent upon the concentration and/or quantum yield of the QDs bound within the microbead 20. By way of a non-limiting example only, when microbeads 20 are doped (i) with an arbitrary 100% QD concentration, and (ii) with a relative 10% QD concentration (i.e., one tenth of the QD concentration), the predetermined maximum range "D" for the 100% QD-doped microbead may be in the approximate order of between about three and about five (~3 to ~5) times higher than that for the 10% QD-doped microbead. In addition, and still by way of example, if the 10% QD-doped microbead provides for a predetermined maximum range "D" of about 300 nanometers (nm), then the 100% QD-doped microbead might provide for a predetermined maximum range "D" of about one micrometer (~1 µm) or more. The predetermined maximum range "D" for any particular microbead 20 may be dependent upon the volume of photon flux within the region 36, and the QD-doping concentration in the microbead 20.

Reference will now be made, briefly, to the method of enhancing fluorescent detection of the target molecules 60 in the test sample (not shown) according to one or more preferred embodiments of the present invention. The method is for use with an irradiating device (not shown) and is, preferably, for use with the system shown in FIGS. 5, 7A-7C and 10. It should, of course, be appreciated that, according to the present invention, the methods may be employed independent of the system described elsewhere herein.

Now, according to the present invention, the method may preferably include steps (a), (b), (c), (d), (e), (f) and/or (g).

In step (a), one or more of the first fluorophores 26 (as shown in FIGS. 5, 7A-7C and 10) are provided. The first fluorophores 26 are adapted for absorption of the EMF radiation 40. The first fluorophores 26 are additionally adapted for emission of the first fluorescent signal 34 following absorption of the EMF radiation 40. As shown in FIG. 1, the first fluorophores 26 are characterized by a first fluorophore absorption profile 28 (substantially encompassing the wavelength(s) of the EMF radiation 40), and by a first fluorophore emission profile 30 (substantially corresponding to the first fluorescent signal 34). The first fluorophore emission profile 30 is itself preferably characterized by a peak intensity 32 at a wavelength of about 580 nanometers (nm).

In step (a), and as best seen in FIGS. 5, 7A and 10, the first fluorophores 26 are bound by microbead 20. In a preferred embodiment, the first fluorophores 26 are provided in the form of the QDs of one or more QD types. For example, in FIG. 10, the QDs are of two different QD types, 26A and 26B. The intensity of the first spectral signal 34 is preferably dependent on the number of QDs bound by the microbead 20. The color of the first spectral signal 34 is preferably dependent upon the size of the QD types, 26A and 26B, bound by the microbead 20.

As may be appreciated from a consideration of FIG. 1, when the first fluorophores 76 are provided in the form of the QDs having their peak intensity 32 at about 580 nanometers (nm), they may be excited, inter alia, by the EMF radiation 40 at a wavelength of about 488 nanometers (nm)—i.e., provided that 488 nm lies, as it preferably does, within the first fluorophore absorption profile 28 characteristic of the first fluorophores 76 (as best seen in FIG. 1).

In step (b), one or more of the second fluorophores 76 (best seen in FIGS. 5, 7C and 10) are provided. The second fluorophores 76 are adapted for absorption of the first incident portion 34A of the first fluorescent signal 34. The second fluorophores 76 are additionally adapted for emission of the second fluorescent signal 84 after absorption of the first fluorescent signal 34 (as may be best appreciated from a consideration of FIGS. 2 and 3).

As best seen in FIG. 3, the second fluorophores 76 are characterized by a second fluorophore absorption profile 78, and by a second fluorophore emission profile 80 (corresponding to the second fluorescent signal 84). As shown in FIG. 2, the second fluorophore absorption profile 78 substantially overlaps with the first fluorophore emission profile 30, to define an overlap region 100. In this context, and for the purposes of this application, "substantially overlaps" means to a degree sufficient for excitation of the affected fluorophores. That is, the first fluorophore emission profile 30 is operative, in its overlap region 100 (with the second fluorophore absorption profile 78), to excite the second fluorophores 76.

As shown in FIG. 4, the second fluorophore emission profile 80 (and the second fluorescent signal 84) is distinguishable from the first fluorophore emission profile 30 (and the first fluorescent signal 34). Preferably, and as may be appreciated from a consideration of FIGS. 1 and 4, the second fluorophore emission profile 80 (best seen in FIG. 4) is substantially removed from—i.e., it does not substantially overlap with—the first fluorophore absorption profile 28 (best seen in FIG. 1). As may be described in considerably greater detail elsewhere herein, the first fluorescent signal 34 and the second fluorescent signal 84 are operatively detectable within the same visible light spectrum (i.e., if the target molecules 60 are present in the test sample).

Step (c) is preferably performed after step (a). In step (c), the BRMs 50 are provided. Preferably, and as best seen in FIG. 10, the BRMs 50 are adapted to operatively bind with the microbeads 20 and the target molecules 60 (if present in the test sample), so as to secure the first fluorophores 26 relative to the target molecules 60.

Preferably, step (d) is performed after step (b). In step (d), the marker molecules 70 are provided. As best seen in FIG. 10, the marker molecules 70 are adapted to operatively bind with the second fluorophores 76 and the target molecules 60 (if present in the test sample). In this manner, the marker molecules 70 secure the second fluorophores 76 relative to the target molecules 60 (if present in the test sample).

Step (e) is preferably performed after at least one, and preferably all, of steps (b) through (d). As may be best appreciated from a consideration of FIG. 10, in step (e), the microbeads 20 containing the first fluorophores 26 are operatively combined with the BRMs 50, the test sample (not shown) potentially containing the target molecules 60, the marker molecules 70, and/or the second fluorophores 76.

Preferably, step (f) is performed after step (e). In step (f), and as shown in FIG. 5, at least the first fluorophores 26 are operatively irradiated with the EMF radiation 40 via the irradiating device (not shown). Preferably, the second fluorophores 76 may also be operatively irradiated with the EMF radiation 40.

Step (g) is preferably performed after step (f). In step (g), and as may be best appreciated from a consideration of FIGS. 4 and 5, the first spectral signal 34 is operatively detected, together with the second spectral signal 84 (if the target molecules 60 are present in the sample).

In one preferred embodiment, and with further reference to FIG. 10, the microbeads 20 may be doped with the first fluorophores 26 in the form of two different QD types, 26A and 26B, to create a specific emission spectrum ("barcode") uniquely identifying a particular one of the microbeads 20 with a specific set of the BRMs 50 bound thereto. The overall intensity and color of the microbead 20 is preferably determined by the amounts, sizes and/or ratios of the different QD types, 26A and 26B, used in the doping process.

FIG. 6 shows the median intensity of emitted wavelengths produced from a series of synthetic microbeads 20 in which the percentage doping with the QDs (i.e., the first fluorophores 26) was varied between about 10% and about 100% of a stock concentrated QD solution. In FIG. 6, the average emission intensity for the series of microbead 20 samples is displayed as measured on a FACSCalibur flow cytometer.

In one preferred embodiment according to the present invention, the microbeads 20 are doped with the QDs (i.e., the first fluorophores 26) which emit the first fluorescent signal 34 with a wavelength centered roughly about 580 nanometers (nm)—such that these microbeads may alternately herein be referred to as QD580 doped microbeads 20. The QD580 doped microbeads 20 may be used, for example, as a substrate in a sandwich nucleic acid or genomic assay (as shown in FIGS. 5 and 7A-7C) or in a sandwich immunoassay according to one or more preferred methods of the present invention. Preferably, the QDs (i.e., the first fluorophores 26) are thus operative to sensitize and/or enhance the emission intensity for the second fluorophores 76 (e.g., Cy5 molecular dyes).

Preferably, and as may be best appreciated from a consideration of FIG. 1, a 488 nm laser (not shown) may be used to excite the QD580 doped microbeads 20. As shown in FIG. 5, the QD580 doped microbeads 20 may be bound to the target molecules 60, which are in turn bound to the marker DNA molecules (i.e., the marker molecules 70). Each of the marker DNA molecules may preferably bear one or more Cy5.5 molecular dyes (DNA-Cy5.5) which provide for an emission towards the red end of the visible light spectrum. FIG. 8 graphs the median dye intensity for the Cy5.5 molecular dyes in conjunction with the median QD intensity of the QD580 doped microbeads.

On excitation with the 488 nm laser, the QDs are selectively excited, and the DNA-Cy5.5 emission is enhanced (with a concomitant increase in its median QD intensity), as may be appreciated from a consideration of FIG. 8.

Compared against this reference line, FIG. 8 also graphs the median dye intensity for FAM molecular dyes (DNA-FAM) bound in conjunction with the marker DNA molecules, the target molecules 60, and the QD580 doped microbeads. The FAM molecular dyes provide for an emission substantially within the green range of the visible light spectrum. Perhaps notably, the FAM molecular dyes are situated generally in the blue (higher energy) direction from the generally yellow-emitting QD580 doped microbeads.

In FIG. 8, the intensity of the DNA-Cy5.5 emission is compared to the intensity of the DNA-FAM emission over a range of median QD intensities. As may be appreciated from a consideration of FIG. 8, the represented data fails to demonstrate a corresponding enhancement and excitation of surface-bound DNA-FAM by QD580-doped microbeads.

The prior art may heretofore have been largely based on the use of second fluorophores 76 situated generally towards the "blue" end of the spectrum relative to the QDs (i.e., the first fluorophores 26). As such, in the prior art, the second fluorophores 76 may have been effectively quenched, with the second fluorescent signal 84 being diminished by the first fluorophore absorption profile 28 and/or the first fluorophore emission profile 30 (shown in FIG. 1) of the QD-doped microbead 20.

In order to provide for enhancement of the second fluorescence signal 84 (and not the previously known opposite quenching effect), it may be generally thought preferable—though perhaps not essential to the working of the present invention—for the second fluorophore emission profile 80 (and thus the second fluorescent signal 84 emitted by the second fluorophores 76) to be located towards the "red" end of the visible light spectrum—i.e., relative to the first fluorescent signal 34 emitted by the first fluorophores 26. It may also be preferable for the first fluorophore emission profile 30 (and thus the first fluorescent signal 34 of the first fluorophores 26) to be located in the yellow range of the visible light spectrum.

It may be appreciated that the graph shown in FIG. 9 illustrates the second fluorophores 76 (preferably, the Cy5 molecular dyes) as being adapted to emit the enhanced second fluorescent signal 84 as a function of QD-doping within the microbeads 20. Preferably, the Cy5 emission intensity may increase to become in the approximate order of over about 200 times brighter when compared to a blank (non-doped) microbead 20 sample. (A lack of controls—e.g., blank microbeads—in prior experiments may have made their results and/or procedures substantially unsuitable for any testing or exploitation of the enhancement effect described herein.) Although not essential to the working of the present invention, it may be believed that the intensity generated by use of the microbead 20 emission, alone, may be about as great as (or greater than) that generated by use of the laser alone.

It is believed that overall fluorescent detection sensitivity may be substantially increased by enhancement of the second fluorophores 76, thus enabling the second fluorophores 76 (whether they be dye molecules or QDs) to be used in conjunction with larger and more intense emission molecules, such as the microbeads 20 referred to herein.

Other modifications and alterations may be used in the design and manufacture of other embodiments according to the present invention without departing from the spirit and scope of the invention, which, is limited only by the accompanying claims of this application. For example, while the above method and system have, in one preferred embodiment, been presented in the context of an immunoassay and a genomic assay, the method and system may be equally applicable to other types of assays (and/or for the detection of other types of target molecules, possibly in other types of test samples).

Additionally, the method and system according to the present invention may preferably be used for a variety of in vitro biomolecular assays including genomic and/or proteomic identification of markers for infectious diseases, cancer, cystic fibrosis and other human veterinary or environmental aliments. Similarly, the method and system according to the present invention may preferably be used for detection of cardiac symptoms and/or detection of biomarkers for cardiac conditions and/or predispositions. The method and system according to the present invention are also preferably adapted for use in medical imaging and other in vivo applications.

In view of all of the foregoing, it is perhaps worthwhile to once again note that the foregoing description has been presented for the purpose of illustration and is not intended to be exhaustive or to limit the invention to the precise form disclosed. Many further modifications and/or variations are possible in light of the teachings herein, as may be apparent to those skilled in the art. It is intended that the scope of the present invention be limited not by this description but only by the accompanying claims.

What is claimed is:

1. A method of enhancing fluorescent detection of target molecules in a test sample, for use with an irradiating device, the method comprising the steps of:

combining one or more first fluorophores and one or more second fluorophores with the test sample, wherein the first fluorophores comprise quantum dots of one or more quantum dot types, so as to secure the first fluorophores and the second fluorophores relative to the target molecules if present in the test sample, and so as to secure the second fluorophores within a predetermined maximum range of the first fluorophores, wherein the predetermined maximum range is less than about 10 micrometers (µm); and irradiating at least the first fluorophores with electromagnetic frequency (EMF) radiation via the irradiating device, such that the first fluorophores absorb the EMF radiation and thereafter emit a first fluorescent signal, such that a radiative flux of the first fluorescent signal is substantially unabated over the predetermined maximum range, and such that if the target molecules are present in the test sample, the second fluorophores absorb a first incident portion of the first fluorescent signal and thereafter emit a second fluorescent signal, with the second fluorescent signal being distinguishable from the first fluorescent signal; such that the first fluorescent signal is operatively detectable, together with the second fluorescent signal if the target molecules are present in the test sample;

wherein the first fluorophores are characterized by a first fluorophore emission profile corresponding to the first fluorescent signal; and wherein the second fluorophores are characterized by a second fluorophore absorption profile which substantially overlaps with the first fluorophore emission profile;

wherein the first fluorophores are bound by microbeads; and further comprising a step of binding biorecognition molecules (BRMs) with the microbeads and the target molecules, so as to as aforesaid secure the first fluorophores relative to the target molecules if present the test sample; and further comprising a step of binding marker molecules with the second fluorophores and the target molecules, so as to as aforesaid secure the second fluoro hones relative to the target molecules if present in the test sample.

2. A method according to claim 1, wherein the first fluorophores are characterized by a first fluorophore absorption profile substantially corresponding to the EMF radiation; and wherein the second fluorophores are characterized by a second fluorophore emission profile, corresponding to the second fluorescent signal, which is substantially removed from the first fluorophore absorption profile.

3. A method according to claim 1, wherein the first fluorophores have a higher emission wavelength than the second fluorophores.

4. A method according to claim 1, for use with a laser as the irradiating device, and wherein the EMF radiation has a wavelength of about 488 nanometers (nm).

5. A method according to claim 1, wherein the predetermined maximum range is in the order of about 300 nanometers (nm).

6. A method according to claim 1, wherein the target molecules are known to be associated with, and wherein the method is for detection of infectious diseases.

7. A method according to claim 1, wherein the target molecules are known to be associated with, and wherein the method is for detection of cancer.

8. A method according to claim 1, wherein the target molecules are known to be associated with, and wherein the method is for detection of cystic fibrosis.

9. A method according to claim 1, for use in a biomolecular assay.

10. A method according to claim 1, wherein the second fluorophores also absorb the EMF radiation, and emit the second fluorescent signal following absorption of the EMF radiation.

11. A method according to claim 1, further comprising a step of combining the microbeads with the BRMs, the test sample, and the second fluorophores.

12. A method according to claim 1, further comprising a step of combining the first fluorophores with the test sample, the marker molecules, and the second fluorophores.

13. A method according claim 1, wherein the second fluorophores also absorb the EMF radiation, and emit the second fluorescent signal following absorption of the EMF radiation; and further comprising a step of irradiating the first fluorophores and the second fluorophores with the EMF radiation via the irradiating device.

14. A method according to claim 1, further comprising a step of operatively detecting the first fluorescent signal, together with the second fluorescent signal if the target molecules are present in the test sample.

15. A system for enhancing fluorescent detection of target molecules in a test sample, for use with an irradiating device, the system comprising:
(a) one or more first fluorophores characterized by an ability to absorb electromagnetic frequency (EMF) radiation, and by an ability to emit a first fluorescent signal following absorption of the EMF radiation, wherein the first fluorophores comprise quantum dots of one or more quantum dot types; and
(b) one or more second fluorophores characterized by an ability to absorb a first incident portion of the first fluorescent signal, and by an ability to emit a second fluorescent signal following absorption of the first incident portion, with the second fluorescent signal being distinguishable from the first fluorescent signal;

wherein the first fluorophores and the second fluorophores are further characterized in that:
(i) when operatively combined with the test sample, the first fluorophores and the second fluorophores are secured relative to the target molecules if present in the test sample, such that the second fluorophores are secured within a predetermined maximum range of the first fluorophores, wherein the predetermined maximum range is less than about 10 micrometers (µm);
(ii) when at least the first fluorophores are operatively irradiated with the EMF radiation via the irradiating device, the first fluorophores emit the first fluorescent signal, such that a radiative flux of the first fluorescent signal is substantially unabated over the predetermined maximum range, and if the target molecules are present in the test sample, the second fluorophores absorb the first incident portion of the first fluorescent signal and emit the second fluorescent signal whereby the first fluorescent signal is operatively detectable, together with the second fluorescent signal if the target molecules are present in the test sample;

wherein the first fluorophores are characterized by a first fluorophore emission profile corresponding to the first fluorescent signal; and the second fluorophores are characterized by a second fluorophore absorption profile which substantially overlaps with the first fluorophore emission profile;

wherein the first fluorophores are bound by microbeads; and further comprising biorecognition molecules (BRMs) characterized by an ability to operatively bind with the microbeads and the target molecules, so as to secure the first fluorophores relative to the target molecules if present in the test sample; and further comprising marker molecules characterized by an ability to operatively bind with the second fluorophores and the target molecules, so as to secure the second fluorophores relative to the target molecules if present in the test sample.

16. A system according to claim 15, wherein the first fluorophores are characterized by a first fluorophore absorption profile substantially corresponding to the EMF radiation and the second fluorophores are characterized by a second fluorophore emission profile, corresponding to the second fluorescent signal, which is substantially removed from the first fluorophore absorption profile.

17. A system according to claim 15, wherein the first fluorophores have a higher emission wavelength than the second fluorophores.

18. A system according to claim 15, for use with a laser as the irradiating device, and wherein the EMF radiation has a wavelength of about 488 nanometers (nm).

19. A system according to claim 15, wherein the predetermined maximum range is in the order of about 300 nanometers (nm).

20. A system according to claim 15, wherein the target molecules are known to be associated with, and wherein the system is for detection of infectious diseases.

21. A system according to claim 15, wherein the target molecules are known to be associated with, and wherein the system is for detection of cancer.

22. A system according to claim 15, wherein the target molecules are known to be associated with, and wherein the system is for detection of cystic fibrosis.

23. A system according to claim 15, for use in a biomolecular assay.

24. A system according to claim 15, wherein the second fluorophores are further characterized by an ability to operatively absorb the EMF radiation, and by an ability to operatively emit the second fluorescent signal following absorption of the EMF radiation.

25. A system according to claim 15, wherein the microbeads are operatively combined with the BRMs, the test sample, and the second fluorophores.

26. A system according to claim 25, wherein the second fluorophores are also operatively adapted for absorption of the EMF radiation, and for emission of the second fluorescent signal following absorption of the EMF radiation; and wherein the first fluorophores and the second fluorophores are operatively irradiated with the EMF radiation via the irradiating device.

27. A system according to claim 15, wherein the first fluorophores are operatively combined with the test sample, the marker molecules, and the second fluorophores.

* * * * *

UNITED STATES PATENT AND TRADEMARK OFFICE
CERTIFICATE OF CORRECTION

PATENT NO.        : 8,551,786 B2
APPLICATION NO.   : 12/668264
DATED             : October 8, 2013
INVENTOR(S)       : Chan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 453 days.

Signed and Sealed this
Fifteenth Day of September, 2015

Michelle K. Lee
*Director of the United States Patent and Trademark Office*